United States Patent
Edlund et al.

(10) Patent No.: US 7,348,163 B2
(45) Date of Patent: Mar. 25, 2008

(54) HUMAN GABA$_B$ RECEPTOR 1 PROMOTERS

(75) Inventors: Anders Edlund, Umeå (SE); Jonas Ekstrand, Sävar (SE); Thore Johansson, Umeå (SE); Göran Leonardsson, London (GB)

(73) Assignee: AstraZeneca AB, Sodertalje (SE)

( * ) Notice: Subject to any disclaimer, the term of this patent is extended or adjusted under 35 U.S.C. 154(b) by 133 days.

(21) Appl. No.: 11/177,000

(22) Filed: Jul. 7, 2005

(65) Prior Publication Data
US 2006/0019345 A1  Jan. 26, 2006

Related U.S. Application Data

(62) Division of application No. 09/622,745, filed as application No. PCT/SE00/00878 on May 4, 2000, now Pat. No. 6,933,124.

(30) Foreign Application Priority Data
May 6, 1999 (SE) .................. 9901659

(51) Int. Cl.
C12P 21/06 (2006.01)
C12N 1/20 (2006.01)
C12N 15/00 (2006.01)
C12N 5/00 (2006.01)
C07H 21/02 (2006.01)

(52) U.S. Cl. ............... 435/69.1; 435/252.3; 435/320.1; 435/325; 435/471; 536/23.1

(58) Field of Classification Search ............... None
See application file for complete search history.

(56) References Cited

FOREIGN PATENT DOCUMENTS

| WO | WO 97/46675 | 12/1997 |
|---|---|---|
| WO | WO 99/21890 | 5/1999 |

OTHER PUBLICATIONS

Mu W and Burt DR. Molecular Brain Research 73:172-180, 1999.*
Peters, H.C. et al., *Mapping, genomic structure, and polymorphisms of the human GABA$_B$R1 receptor gene: evaluation of its involvement in idiopathic generalized epilepsy*, Neurogenetics, vol. 2, pp. 47-54 (1998).
Younger, R., EMBL Database/Genbank/DBJ, Accession No. AL031983, "Direct Submission" (submitted Jan. 20, 1999).

* cited by examiner

*Primary Examiner*—Robert S. Landsman
(74) *Attorney, Agent, or Firm*—White & Case LLP

(57) ABSTRACT

The present invention relates to nucleic acid molecules constituting GABA$_B$ receptor 1 promoters P1a and/or P1b, and to methods for screening for compounds which are modulators of GABA$_B$ receptor 1 transcription, said methods comprising the use of nucleic acid molecules constituting GABA$_B$ receptor P1a and/or P1b promoters.

21 Claims, 6 Drawing Sheets

SEQUENCE LISTING

<160> NUMBER OF SEQ ID NOS: 26

<210> SEQ ID NO 1
<211> LENGTH: 3903
<212> TYPE: DNA
<213> ORGANISM: Homo sapiens
<220> FEATURE:
<221> NAME/KEY: Misc_signal
<222> LOCATION: (1497)..(1503)

```
<223> OTHER INFORMATION: P1a
<220> FEATURE:
<221> NAME/KEY: GC_signal
<222> LOCATION: (3009)..(3016)
<223> OTHER INFORMATION: Complement
<220> FEATURE:
<221> NAME/KEY: GC_signal
<222> LOCATION: (3037)..(3044)
<220> FEATURE:
<221> NAME/KEY: GC_signal
<222> LOCATION: (3116)..(3123)
<223> OTHER INFORMATION: Complement

<400> SEQUENCE: 1
gatcatatta atttgaaggt ggcggggcag gatggttctg tggtgcagtt taagattaag      60
aggcatacac cacttagtaa actaatgaaa gcctattgtg aacgacaggg attgtcaatg    120
aggcagatca gattccgatt cgacgggcaa ccaatgaaac agacacacct gcacagttgg    180
aaatggagga tgaagataca attgatgtgt ccaacagca gacgggaggt gtctactgaa     240 aagggaaccct gcttctttac tccagaactc tgttctttaa agaccaagat tacattctca   300
attagaaaac tgcaatttgc ttccaccaca tcctgactac taccgtatag ttttctctat    360
tctttcattt cccccttccc cattccttta ctgtacataa agtaactggt atatgtgcac    420
aagcatatta ctttttttt ttaaaactaa acagccaatg gtatgttttg attgacatca     480
agtggagacg gggggaaaa tactgattct gtgaaaatac cccctttctc cattagtggc     540
atgctcattc agctcttatc tttatattcc agtaagttat tttgctctca ctgttttaac   600
aacaacaaca aaaaacaac aacataaaaa tccttgcata ccttgttcaa ttggagaatt     660
ttaatgtttt tcatttatca ttgtaaaacc aaggacaatt ttataacttt tttgtactta   720
gctgttacat gcagagcaat ctgtctttaa gtagggataa attactctaa aacaaaaaag   780
aatcctagat agttttccct tcaagtcaag cgtcttgttg tttaaataaa cttcttgttt   840
aaaaaaaaaa aaagtaaaaa agaaaagtta tgcaacaatt aatggcccag aggcaatcct   900
tgttaacatt tgatgcatc ttttagctgt tttttttttt tttttttttt ttgactgagt    960
ttgactcttg tcacccaggc tgaagtgcaa tggcatggca tgatcttggc tcactgcaac  1020
ctccgcctcc cgggttcaag tgattctcct gcctcagcct cctgagtagc taggattacg  1080
ggcatgcacc accatgcctg gctaattttg tattttagt agagttgggg cttctccaca   1140
ctggtcaggc tggtctcgaa ctcccaacct caggtgataa gggaaggggc actattgaca  1200
tttatggttg gggcagaggt gtaagatatt cttcaaagca ctacctacat gttgaagaat  1260
tgttcctcac ccagattctc aaaagtcccc caggacattc acgtagtgaa aacctgtgtt  1320
taattatctg agcctataac ttaatacagt tttaaaattt tttttaaat atacagtgaa   1380 cttttctagga atgcaattat agttgtgtgt aaaattaggg aaaattaact ttgctaccaa  1440
gagttgttca acattttgtt aaatcacttc attgatggca acatgctgga ggtagttgag  1500
tcaccaactc agcacctgga tcagcctgtg ttggtagcag tttcatcccc gtggttctgt   1560
gaataggtgg aagcatctgc ttactccatc aggacttcta gggtagtcgg gccttggcac  1620
tcacacatta aaatactgtt tatgttattt tattgcaagt tacttttctt tcatttcccc   1680
tttacgttac agaaagggaa gcattttgct ttctgtttaa agttgtgtat gtaggtaggt  1740
tatatcatct awgactttct ctccctcctt ccctttcttt ttgtttgaga tggagtcttg   1800
ctctgtcacc caggctggag tgcagtggtg cgatcttggc tcactgcaac ctctgcctcc  1860
cgggttcaag cgattctggt gtctcagctg ggattacagg cgcacaccat cacaccacgc  1920
```

```
taatttttct attttttagta gagatggggt ttcgccatgc tggccaggcc aggctggtct   1980
caaactcctg agctcaagtg atcagtccgc ctcggcctcc caaagttctg ggatttcagg   2040
cgtgagcctc atctatgaat ctcaatttag gacagtaaaa gtgtcattac aaaaatattt   2100
attgtaaaaa agggttggag gttgagaatc tcaattctag tcagtctctc agtgtttggt   2160
ttcttcctac cattttcccc cctaggacca gccagaaagc agcttttttt ttgtcccccc   2220
caacaaggag cccactgttt cctctcccag cccaaactca ggcctacgaa caacaacagc   2280
actacacaca cacacacaca cacacacaca cacacacaca caccccctcca cttcaaggta   2340
tagccaagag cttctggagc cgtcaaaaag gtctgtacct gctgtcttta gagcttccag   2400
tttgcccttg gtcaagaaat actgtttgct aggctctgct ggagtacatc aggtaatact   2460
ggcttctaaa ccaccctgag gttctttttct cttgtccttt tactcccttc gtacttcaat   2520
ttctctcctt gatgtccccc tccctgtttt gttttttgcc tccaatccgt tctgcgcgtt   2580
ccctgcagag caggcgagta gcaatgctgc tggaccatgg agctgctcta gtctcccaga   2640
aatctcttct acacccaacc cttcttgcgc ttaggtggtc ctcagtcccc ctcccccacc   2700
tccttctgac ccaggcttct ttctcgcccct ccggtcgcag ttctcctggg catctgcctc   2760
tgcctctctc ctctcacccg gatctagggc tgccttctct ttgtgcagcc gtctttctcc   2820
accttcatcc cagactccct gtctcagcgc cagctcctct gcctttggct cgggttccct   2880
ctcccccacc ccagcttcca gttgtttggc ccgcaggtcc ctcggcagtg accggcgccc   2940
cccgacgagt gcgtgtgcac cagggcacct ccctctcccc cacctctcag ccccgcgcct   3000
ctccaccgcc cgccccaccg cgctgtgggc ggtccagggc ggggctggga tccggggcgg   3060
ctcccggggc tcgggttgtg ggaggcgccc tctcccccggt cttccctct cttccccccg   3120
ccctgccttc ccttgcaccc tccttcttcc ctccgcccgg gagctctccc tggtcccccgg   3180
cgccgcctcc ttccctcccg gctccccgct ccccgctccc gtggctgccg ccgcccccggg   3240
gaagaagaga caggggtggg gtttggggga agcgagagag gaggggagag accctggcca   3300
ggctggagcc tggattcgag gggaggaggg acgggaggag gagaaaggtg gaggagaagg   3360
gaggggggag cggggaggag cggccgggcc tggggccttg aggcccgggg agagccgggg   3420
agccgggccc gcgcgccgag gtaagagcca gggccccggg ttagcagggc tcggagaggg   3480
ggcgcgcggc gtggtgggggg aggggcagt gggcgcaggg cccagctggg ggaagcgggg   3540
ctggggggaga ggaggaaccg cggggatgga atcggggagc gctgaggcgg ccgatgccgg   3600
gagcgtgggt aagccaggct tctgcgagcc gcggggcccg ggggagagga ggtggtgaga   3660
ggtggagtcc gggagggttg ggggccgagg gaggcaggag gagggtgggg acaggctttc   3720
tctcctcctc tccccccacc ccgcgcgggg ctccgccccc gcctcctccg cggggcgctc   3780
tcttggtccc caggctgagc ccggtcggag cctgcgaggc aaccggcaag aggtcgagta   3840
gtctcccgggt gcgggccgcg ccggcggggc tcggtccagt cctcatggcc gcctctcact   3900
tag                                                                3903
```

```
<210> SEQ ID NO 2
<211> LENGTH: 4594
<212> TYPE: DNA
<213> ORGANISM: Homo sapiens
<220> FEATURE:
<221> NAME/KEY: Misc_binding
<222> LOCATION: (3844)..(3851)
<223> OTHER INFORMATION: AP-2
<220> FEATURE:
<221> NAME/KEY: GC_signal
```

```
<222> LOCATION: (4080)..(4087)
<223> OTHER INFORMATION: Complement
<220> FEATURE:
<221> NAME/KEY: GC_signal
<222> LOCATION: (4196)..(4205)
<223> OTHER INFORMATION: Complement
<220> FEATURE:
<221> NAME/KEY: GC_signal
<222> LOCATION: (4241)..(4249)
<223> OTHER INFORMATION: Complement
<220> FEATURE:
<221> NAME/KEY: GC_signal
<222> LOCATION: (4272)..(4279)
<223> OTHER INFORMATION: Complement
<220> FEATURE:
<221> NAME/KEY: Misc_binding
<222> LOCATION: (4308)..(4315)
<223> OTHER INFORMATION: CRE
<220> FEATURE:
<221> NAME/KEY: Misc_binding
<222> LOCATION: (4375)..(4381)
<223> OTHER INFORMATION: Initiator

<400> SEQUENCE: 2
```

| | | | | | |
|---|---|---|---|---|---|
| atgttgctgc | tgctgctact | ggcgccactc | ttcctccgcc | cccgggcgc | gggcggggcg | 60 |
| cagaccccca | acgccacctc | agaaggtgca | tccttcttcg | acgacctccg | gccctccttc | 120 |
| gctccacttc | cctttccctg | catctcctca | tttctggtcc | tcatcactat | cccatcagtc | 180 |
| ccacatatca | tcccggtctg | gcaacccctt | ctgctcggcc | cgactttact | actgctgacc | 240 |
| tccttctgtc | accccacgtt | actatccagc | acctcttttc | tctgcccaca | ttgctacact | 300 |
| ataccacctt | cctgtgcatt | ttctccgcct | caatcccctt | tcccagcccc | acattactac | 360 |
| ctcaattact | ccctttcctt | ggtcccactt | tgctgtccag | atgatcttat | tagcctccct | 420 |
| ttatcctcct | atcctaattc | aactggaata | tcctcattta | gccttttttt | ttaaagaaaa | 480 |
| gctccaccca | catatcatac | ccttcatgat | ttcttaatta | cttttctttc | ttacctccac | 540 |
| ccagcaccct | tccctcccca | cttgtgggtt | ctctcatcag | ctttaaccct | ggcccttac | 600 |
| tctctgtcct | ttagccaggg | gatctgtacc | tgtccccact | cccaccctct | agtgccccat | 660 |
| ccctcttcct | ctgtccccag | cctgcccaca | gaccacgccc | tactctcccc | ttcctcccac | 720 |
| tggggagcct | gccttttcct | ctttcccacc | attcctctct | gtatgcctcc | ccgactcacc | 780 |
| ccttaggttg | ccagatcata | cacccgccct | gggaagggg | catcaggtac | cggggcctga | 840 |
| ctcgggacca | ggtgaaggct | atcaacttcc | tgccagtgga | ctatgagatt | gagtatgtgt | 900 |
| gccgggggga | gcgcgaggtg | gtggggccca | aggtccgcaa | gtgcctggcc | aacggctcct | 960 |
| ggacagatat | ggacacaccc | agccgctgtg | gtgagtagcc | tcggaagccc | ctcccctctt | 1020 |
| caagactatt | ccttttcctg | ccgcaaactt | agcattactg | cttgcaagtc | agcacttaa | 1080 |
| atccagtata | ccaaaattca | caaatacatt | tattgaatga | ctactacata | agagcaattt | 1140 |
| tgctctgtgc | ggttggaggt | agtagagcta | gcagcctgca | cagttcattt | catcctccct | 1200 |
| tcattaggcc | actgatcatt | ggcctataac | attgataatt | catcttgtca | gttattctct | 1260 |
| ttgaggatca | ttagtggcag | atgatgacaa | aaaaattcta | aaatgatttc | atcacatttt | 1320 |
| tgaatacctc | tgtcaccaac | ccagagacca | tatgcccaag | aaacaaaagc | cagtttaata | 1380 |
| ttaatagaag | ccaactataa | taagaaaagc | aaatctgatt | gtgcatccaa | agttatatac | 1440 |
| atctacatat | ttcaaagcca | gagaaccgcc | cactgtagct | gactttgaag | agatcccatt | 1500 |
| ttgtgtgctt | atagccccat | cttgggttcc | taaaatggta | attttttttt | tcttttggga | 1560 |
| atgtgtggat | gcttgcacag | gtaagggagg | attggaagat | aggtaggcaa | atccttttca | 1620 |

```
catgtgattt tctttagagc aggatgcttg tggacccaaa cctgcacctg agtccctgc    1680
tctttaaagg gaaagagcct tcttcaactc gcctctcttc ttatttttcct atctctccac  1740
agtccgaatc tgctccaagt cttatttgac cctggaaaat gggaaggttt tcctgacggg   1800
tggggacctc ccagctctgg acggagcccg ggtggatttc cggtgtgacc ccgacttcca   1860
tctggtgggc agctcccgga gcatctgtag tcagggccag tggagcaccc ccaagcccca   1920
ctgccagggt gaggggaaca gctgcctgca tgcagctgat gaggacgctt gtgtgaggat   1980
gggagtgggg tgggaatgga taatgggaaa gaatggagag ctataaaaat gtgggggagg   2040
acactggaaa ggggagatga aagtcccttt ttcctccatc acctgcctca aacttcctct   2100
tgcagtcccc ggtatcctct gtaggttggg ggcttccttc ctttacccttt taaaaaaatc  2160
ttcctgctcc cgattcttag acctcacgtt ttctcttttc ctttatgaat ctcacctctc   2220
tcaccttctt caggttttaaa tactccaatt ttcccttttct ctaaacttag aaatttccat 2280
gcatcaccct cttctagaat tcatccctca ccattcctta tataattgat ttattgtaaa   2340
gactcagaaa taaatcaaac attctactaa gaaaaattga aaggggagc tctgggggtg    2400
gaaacatatt agggtaaaag acttaaaatt ggaggcagca ttatcagaag atgaagaaca   2460
actcagggat ggggtgggaa gaagacaggt ccttttctgk acttcctaga caacctccat   2520
tattccctaa gggaatcagt gttgtgtctg tctacyyttt tttttttttt tttgccacgt   2580
aattttacaa actctcccctt ttctaggcac ccgaactctc tgccatcttc tctcctggga  2640
tgcagtcatc ccatttgtat gcctcatact tcctctaccc tggtagattc tttcaagatc   2700
cttgggcttt actttcctca cataactcag ttattctgct tctagtttac catttttattc  2760
tggaaattga gagtcccatc caggggtgga cttatgacac tactgaaact tagacttcaa   2820
ggttcctcac ctacagggcc ctcttcctgt gctctaataa tatagagggc tcgatggata   2880
tgtgttcata tggtaacagg cttttgtaaa aattgcagaa ataagatttt aacagcaatt   2940
gcttaaagcc aattgtatgt gtaattttttt tcttaaaga ctcccaattt tgtaatattc   3000
aggcaccaca gaaccaagat ctgccccaaa cttagctatt ggcattcccg tctcaaattc   3060
tgttgtccta tgaaaaatcg aagaagaaaa taagtcctga ccccttacc cccagaccca    3120
ccttgttctt atccccaggc accctccccct cagaaacgca ggcttctgct ctccccggtc  3180
ttcagcatgg acaggtgtgg gagggggctg gggatcaggc cagggaagct gggcgccagt   3240
ggtaactctt ctctgatccc cgtctttcct gctgccagtg aatcgaacgc cacactcagg   3300
tgagatgaga aacccttacc gcgcgcactg caatgccctc cccttcactc tgcaccctcc   3360
accccctga aattctgccc ttaggctacg gggcgtcgtc ctttcgcacc ttccccaacc    3420
caccccagtt tgcggccacc cccttccctc cctacctgtt tcctgcctcc agtcccggtt   3480
ttccacgagg ctgcggtctc tccttgtccc tgcttggcta cacttccctg ggctccacct   3540
cctcccagac tgagcctcgc cggtgtcagg cagagcccag cagarggcgg cagggtgctg   3600
ggagaccctg agctcccacc acgttttccc ctgtggggtt ccttgcgacc ttcgctggaa   3660
cctttttccag cctgctgcct cctaggattt cacctaatgg actttctcag cctgtcccac  3720
ccatcccaac cctggccagg cctctcgcgc tcttccccac atcttttcct tccgtgtacc   3780
ccttccctcg tcttttctca attccatgtc ctgtctccct ttcttaggct tctgtctacc   3840
cagccccagg ctcccttcca cgaccccacc actccctcaa accagcctcc cttccgtacc   3900
caactcgttc cctccaaaac cgtttcctct ccccacatc ctcagtgctt cactgtatcg    3960
actcatactc ccacttcaga cctcaggcgc cagccccgtt tctctcccgt cccactcgca   4020
```

-continued

```
tccttccctt cctaccctgg ttcctccgtg cttcagcctc ccgcggctcc ctccgcccac   4080
cccgccctcc tggcacgccc cgtccccatt tctcctcccc tcgggtcccc ttaagtgaga   4140
tccctccctt cctctttcgt tcctttcctc ctcgaggttg catcccccct cccctccccg   4200
cccctccgac tgtcgctccc acctcggcgc tcgcttccct ccccgccccc ttcctgcctc   4260
cccagctccc gcccgccccc ccaccccccg ctgccgcgcg ccgcccgtga cgtcagagcc   4320
ccctcccagc cccacatctc cctcctgctc ctcctcctcc cctccgtcgg tcagtcagtc   4380
cgcgaggaga gtccgcggtg gcggcgacgg tggcgagagc cgcgggggcc gtaggaagcc   4440
aaccttccct gcttctccgg ggccctcgcc ccctcctccc cacaaaatca gggatggagg   4500
cgcctccccg gcaccctctt agcagccctc cccgggaaaa gtgtcccccc tgagctccta   4560
acgctcccca acagctaccc ctgcccccca cgcc                                4594

<210> SEQ ID NO 3
<211> LENGTH: 23
<212> TYPE: DNA
<213> ORGANISM: Artificial
<220> FEATURE:
<223> OTHER INFORMATION: HindIII site fused to P1a seq 3440-3424

<400> SEQUENCE: 3
aagcttctcg gcgcgcgggc ccg                                              23

<210> SEQ ID NO 4
<211> LENGTH: 24
<212> TYPE: DNA
<213> ORGANISM: Artificial
<220> FEATURE:
<223> OTHER INFORMATION: NheI fused to P1a  sequence 2341-2362

<400> SEQUENCE: 4
gctagccaag agcttctgga gccg                                             24

<210> SEQ ID NO 5
<211> LENGTH: 25
<212> TYPE: DNA
<213> ORGANISM: Artificial
<220> FEATURE:
<223> OTHER INFORMATION: NheI fused to P1a 720-741

<400> SEQUENCE: 5
gctagctgtt acatgcagag caatc                                            25

<210> SEQ ID NO 6
<211> LENGTH: 21
<212> TYPE: DNA
<213> ORGANISM: Artificial
<220> FEATURE:
<223> OTHER INFORMATION: HindIII site fused to P1b sequence 4439-4421

<400> SEQUENCE: 6
aagcttccta cggcccccgc g                                                21

<210> SEQ ID NO 7
<211> LENGTH: 24
<212> TYPE: DNA
<213> ORGANISM: Artificial
<220> FEATURE:
<223> OTHER INFORMATION: NheI site fused to P1b sequence 3321-3340

<400> SEQUENCE: 7
```

```
gctagcgcgc actgcaatgc cctc                                          24
```

<210> SEQ ID NO 8
<211> LENGTH: 26
<212> TYPE: DNA
<213> ORGANISM: Artificial
<220> FEATURE:
<223> OTHER INFORMATION: P R 1b Cre Fwd

<400> SEQUENCE: 8

```
cgccgcccgt ttggtcagag ccccct                                        26
```

<210> SEQ ID NO 9
<211> LENGTH: 26
<212> TYPE: DNA
<213> ORGANISM: Artificial
<220> FEATURE:
<223> OTHER INFORMATION: P R 1b Cre Rev

<400> SEQUENCE: 9

```
aggggggctct gaccaaacgg gcggcg                                       26
```

<210> SEQ ID NO 10
<211> LENGTH: 26
<212> TYPE: DNA
<213> ORGANISM: Artificial
<220> FEATURE:
<223> OTHER INFORMATION: P R 1a GCI Fwd

<400> SEQUENCE: 10

```
ctctcttccc ccctaactgc cttccc                                        26
```

<210> SEQ ID NO 11
<211> LENGTH: 26
<212> TYPE: DNA
<213> ORGANISM: Artificial
<220> FEATURE:
<223> OTHER INFORMATION: P R 1a GCI Rev

<400> SEQUENCE: 11

```
gggaaggcag ttaggggga agagag                                         26
```

<210> SEQ ID NO 12
<211> LENGTH: 26
<212> TYPE: DNA
<213> ORGANISM: Artificial
<220> FEATURE:
<223> OTHER INFORMATION: P R 1a GCII Fwd

<400> SEQUENCE: 12

```
ggcggtccag ttaggggctg ggatcc                                        26
```

<210> SEQ ID NO 13
<211> LENGTH: 26
<212> TYPE: DNA
<213> ORGANISM: Artificial
<220> FEATURE:
<223> OTHER INFORMATION: P R 1a GCII Rev

<400> SEQUENCE: 13

```
ggatcccagc ccctaactgg accgcc                                        26
```

<210> SEQ ID NO 14
<211> LENGTH: 30
<212> TYPE: DNA
<213> ORGANISM: Artificial

```
<220> FEATURE:
<223> OTHER INFORMATION: P R 1a GCIII Fwd

<400> SEQUENCE: 14
cctctccacc gccctaacca ccgcgctgtg                              30

<210> SEQ ID NO 15
<211> LENGTH: 30
<212> TYPE: DNA
<213> ORGANISM: Artificial
<220> FEATURE:
<223> OTHER INFORMATION: P R 1a GCIII Rev

<400> SEQUENCE: 15
cacagcgcgg tggttagggc ggtggagagg                              30

<210> SEQ ID NO 16
<211> LENGTH: 28
<212> TYPE: DNA
<213> ORGANISM: Artificial
<220> FEATURE:
<223> OTHER INFORMATION: P R 1b GCIV Fwd

<400> SEQUENCE: 16
ccccagctcc cgccctaacc cccacccc                                28

<210> SEQ ID NO 17
<211> LENGTH: 28
<212> TYPE: DNA
<213> ORGANISM: Artificial
<220> FEATURE:
<223> OTHER INFORMATION: P R 1b GCIV Rev

<400> SEQUENCE: 17
ggggtggggg ttagggcggg agctgggg                                28

<210> SEQ ID NO 18
<211> LENGTH: 27
<212> TYPE: DNA
<213> ORGANISM: Artificial
<220> FEATURE:
<223> OTHER INFORMATION: P R 1b GCV Fwd

<400> SEQUENCE: 18
cgcttccctc ccctaaccct tcctgcc                                 27

<210> SEQ ID NO 19
<211> LENGTH: 27
<212> TYPE: DNA
<213> ORGANISM: Artificial
<220> FEATURE:
<223> OTHER INFORMATION: P R 1b GCV Rev

<400> SEQUENCE: 19
ggcaggaagg gttaggggag ggaagcg                                 27

<210> SEQ ID NO 20
<211> LENGTH: 27
<212> TYPE: DNA
<213> ORGANISM: Artificial
<220> FEATURE:
<223> OTHER INFORMATION: P R 1b GCVI Fwd

<400> SEQUENCE: 20
ccctcccctc ccctaacctc cgactgt                                 27
```

```
<210> SEQ ID NO 21
<211> LENGTH: 27
<212> TYPE: DNA
<213> ORGANISM: Artificial
<220> FEATURE:
<223> OTHER INFORMATION: P R 1b GCVI Rev

<400> SEQUENCE: 21
acagtcggag gttaggggag gggaggg                                        27

<210> SEQ ID NO 22
<211> LENGTH: 26
<212> TYPE: DNA
<213> ORGANISM: Artificial
<220> FEATURE:
<223> OTHER INFORMATION: P R 1b GCVII Fwd

<400> SEQUENCE: 22
ctccgcccac ccctaactcc tggcac                                         26

<210> SEQ ID NO 23
<211> LENGTH: 26
<212> TYPE: DNA
<213> ORGANISM: Artificial
<220> FEATURE:
<223> OTHER INFORMATION: P R 1b GCVII Rev

<400> SEQUENCE: 23
gtgccaggag ttaggggtgg gcggag                                         26

<210> SEQ ID NO 24
<211> LENGTH: 28
<212> TYPE: DNA
<213> ORGANISM: Artificial
<220> FEATURE:
<223> OTHER INFORMATION: P R 1b GCIVd Fwd

<400> SEQUENCE: 24
ccccagctcc ctaactaacc cccacccc                                       28

<210> SEQ ID NO 25
<211> LENGTH: 28
<212> TYPE: DNA
<213> ORGANISM: Artificial
<220> FEATURE:
<223> OTHER INFORMATION: P R 1b GCIVd Rev

<400> SEQUENCE: 25
ggggtggggg ttagttaggg agctgggg                                       28

<210> SEQ ID NO 26
<211> LENGTH: 26
<212> TYPE: DNA
<213> ORGANISM: Artificial
<220> FEATURE:
<223> OTHER INFORMATION: P 1 b consensus CRE sequence

<400> SEQUENCE: 26
cgccgcccgt gacgtcagag cccct                                          26
```

HUMAN GABA$_B$ RECEPTOR 1 PROMOTERS

This application is a divisional of U.S. application Ser. No. 09/622,745, filed Aug. 22, 2000, now U.S. Pat. No. 6,933,124, which is the National Stage of International Application No. PCT/SE00/00878, filed May 4, 2000.

FIELD OF THE INVENTION

The present invention relates to nucleic acid molecules constituting GABA$_B$ receptor 1 promoters P1a and/or P1b, and to methods for screening for compounds which are modulators of GABA$_B$ receptor 1 transcription, said methods comprising the use of nucleic acid molecules constituting GABA$_B$ receptor P1a and/or P1b promoters.

BACKGROUND

GABA$_B$ Receptor 1

GABA (γ-aminobutyric acid) is an endogenous neurotransmitter in the central and peripheral nervous systems. Receptors for GABA have traditionally been divided into GABA$_A$ and GABA$_B$ receptor subtypes. GABA$_B$ receptors (for a review see Kerr, D.I.B. and Ong, J. (1995) Pharmac. Ther. vol. 67, pp. 187-246) belong to the superfamily of G-protein coupled receptors. GABA$_B$ receptor agonists are described as being of use in the treatment of CNS disorders, such as muscle relaxation in spinal spasticity, cardiovascular disorders, asthma, gut motility disorders such as irritable bowel syndrome and as prokinetic and anti-tussive agents. GABA$_B$ receptor agonists have also been disclosed as useful in the treatment of emesis (WO 96/11680) and reflux disease (WO 98/11885).

The cloning of the cDNA encoding the rat GABA$_B$ receptors splice isoforms GABA$_B$R1a and GABA$_B$R1b is disclosed by Kaupmann et al. (1997) Nature, vol. 386, 239-246. The mature rat GABA$_B$R1b differed from GABA$_B$R1a in that the N-terminal 147 residues were replaced by 18 different residues. It was presumed that the rat GABA$_B$R1a and -b receptor variants are derived from the same gene by alternative splicing.

The cloning of the cDNA encoding the human GABA$_B$ receptor GABA$_B$R1b is disclosed in WO 97/46675.

The cloning of the human GABA$_B$ receptor 1 gene and the elucidation of the exon-intron organization is in part or fully disclosed in PCT/SE98/01947, in EMBL HS271M21 (GenBank AL031983), EMBL AJ010170 to AJ010191, in Peters, H C et al., Neurogenetics 2; 47-54 (1998) and in Goei, V L et al. Biological Psychiatry. 44; 659-66 (1998). The human GABA$_B$ receptor 1 gene consists of 23 exons, spanning over a distance of 30 kb (FIG. 1). The elucidation of the gene organization revealed that the human GABA$_B$R1a and GABA$_B$R1b are splice variants encoded by a single gene. The GABA$_B$R1a and GABA$_B$R1b isoforms are differentially expressed, at least in the rat (Kaupmann et al. (1997) Nature, vol. 386, 239-246). The physiological consequences of multiple GABA$_B$ receptor 1 splice isoforms has not yet been determined, but their existence constitute an opportunity for the development of specific pharmaceutical agents.

GABA$_B$ Receptor 2

Based on its homology with the mammalian GABA$_B$R1 cDNA, a second member of the GABA$_B$ receptor family was identified (Jones, K A et al., Nature 396; 674-679 (1998), White, J A et al., Nature 396; 679-682 (1998), Kaupmann, K et al., Nature 396; 683-687 (1998), WO 99/20751). The corresponding protein, GABA$_B$R2, forms heteromers with GABA$_B$R1a and R1b, resulting in cell surface expression of a functional GABA B receptor (Kuner, R et al. Science 283, 74-77 (1999)). At least in recombinant expression systems, GABA$_B$R1 and R2 coexpression is necessary for the formation of a functional GABA$_B$ receptor. Jones et al. (Nature 396; 674-679 (1998)) disclosed that a GABA$_B$R1: GABA$_B$R2 stochiometry of 1:1 is an optimal ratio for successful cell surface expression of a ligand binding and functional GABA$_B$ receptor. Thus, modulating GABA$_B$R1 expression could alter the stochiometry between GABA$_B$R1 and other interacting proteins and be a means to regulate signaling through GABA$_B$ receptors and thereby interfere with various physiological processes.

Transcriptional Regulation

Gene regulation is mediated by specific DNA elements in the promoter that directs binding of transcription factors, which thereby mediate transcription of the gene. Eukaryotic transcription factors can be divided in two main groups i) basal transcription factors that interact with promoter sequences proximal to the start of transcription, thereby initiating transcription upon recruitment of RNA polymerase II and ii) transcription factors that bind to specific distal promoter elements, thereby modulating the transcription upon contact with the basal transcription machinery. The DNA sequence that directs the start of transcription in most eukaryotic genes is the TATA-box, which is often located approximately 30 base pairs upstream from the start of transcription. However, the TATA-box is not a prerequisite for initiation of transcription as there are many promoters, including the GABA$_B$R1 promoters described in this study, that lack a TATA-box. A fundamental physiological process in the eukaryotic organism is that cells can communicate with their environment and respond to extracellular stimuli through signaling molecules, such as hormones and growth factors. The final event for such signaling is the binding of transcription factors to specific distal promoter elements leading to for example up-regulated or tissue specific gene expression. Because of their regulatory role, signaling molecules are putative targets for screening of therapeutic agents. The presence of two distinct and differentially regulated promoters within the human GABA$_B$ receptor 1 gene, disclosed in this patent application, makes it possible to screen for therapeutic agents selectively regulating expression of GABA$_B$ receptor 1a and 1b-type splice isoforms.

Indications

Compounds which are modulators of GABA$_B$ receptor 1 transcription are potentially useful in the treatment of disorders which are related to neurally-controlled physiological responses regulated by GABA$_B$ receptors, e.g. CNS disorders such as muscle relaxation in spinal spasticity, Alzheimer's disease and other dementias, psychiatric and neurological disorders such as depression, anxiety and epilepsy, cardiovascular disorders, asthma, gut motility disorders such as irritable bowel syndrome, emesis and reflux disease. In some humans, the lower esophageal sphincter (LES) is prone to relaxing more frequently than in other humans. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current therapy has aimed at reducing gastric acid secretion, or by reducing esophageal acid exposure by enhancing esophageal clearance, lower esophageal sphincter tone and gastric emptying. The major mechanism behind reflux has been considered to depend on a hypotonic lower esophageal sphincter. However, recent research (e.g. Holloway & Dent (1990) Gastroenterol. Clin. N. Amer. 19, 517-535) has shown that most reflux episodes occur during transient lower esophageal sphincter relaxations (TLESR), i.e. relaxations not triggered by swallows. It has also been shown that gastric acid secretion usually is normal in patients with GERD. Consequently, there is a need for compounds which reduce the incidence of TLESR and thereby prevent reflux.

DESCRIPTION OF THE INVENTION

This invention relates to nucleic acid molecules constituting $GABA_B$ receptor 1 promoters and fragments of said promoters. By $GABA_B$ receptor 1 promoters is understood the nucleic acids sequences upstream of the ATG translation initiation codon of $GABA_B$ receptor 1a of the $GABA_B$ receptor 1 gene, designated P1a, and the nucleic acids sequences upstream of the ATG translation initiation codon of $GABA_B$ recpetor 1b of the $GABA_B$ receptor 1 gene, designated P1b, as illustrated in FIG. 1.

In the present context the term "promoter" is meant to include core promoter sequences proximal to the start of transcription and upstream promoter elements which bind constitutively active transcription factors, as well as distal promoter elements which bind specific transcription factors.

Accordingly, the present invention provides a nucleic acid molecule constituting a human $GABA_B$ receptor 1 promoter P1a, or a functionally equivalent modified form thereof, or active fragments thereof. The present invention also provides a nucleic acid molecule constituting a human $GABA_B$ receptor 1 promoter P1b, or a functionally equivalent modified form thereof, or active fragments thereof. By a functionally equivalent modified form is understood nucleic acids modified from the original sequence that can bind transcription factors. By active fragments of the promoters is understood nucleic acid fragments that can bind transcription factors.

In preferred forms of the invention the said nucleic acid molecule is selected from:
(a) a nucleic acid molecule comprising a nucleotide sequence set forth as SEQ ID NO: 1;
(b) a nucleic acid molecule comprising a nucleotide sequence capable of hybridizing, under stringent conditions, to a nucleotide sequence complementary to the DNA molecule as defined in (a).

In other preferred forms of the invention the said nucleic acid molecule is selected from:
(a) a nucleic acid molecule comprising a nucleotide sequence set forth as SEQ ID NO: 2;
(b) a nucleic acid molecule comprising a nucleotide sequence capable of hybridizing, under stringent conditions, to a nucleotide sequence complementary to the DNA molecule as defined in (a).

In another preferred form of the invention the said nucleic acid molecule may be a nucleic acid molecule constituting a human $GABA_B$ receptor 1 promoter P1a, or a functionally equivalent modified form thereof, or active fragments thereof, in combination with a nucleic acid molecule constituting a human $GABA_B$ receptor 1 promoter P1b, or a functionally equivalent modified form thereof, or active fragments thereof.

In another preferred form of the invention the said nucleic acid molecule may be a nucleic acid molecule selected from:
(a) a nucleic acid molecule comprising a nucleotide sequence set forth as SEQ ID NO: 1;
(b) a nucleic acid molecule comprising a nucleotide sequence capable of hybridizing, under stringent conditions, to a nucleotide sequence complementary to the DNA molecule as defined in (a);
in combination with a nucleic acid molecule is selected from:
(a) a nucleic acid molecule comprising a nucleotide sequence set forth as SEQ ID NO: 2;
(b) a nucleic acid molecule comprising a nucleotide sequence capable of hybridizing, under stringent conditions, to a nucleotide sequence complementary to the DNA molecule as defined in (a).

It should thus be understood that the nucleic acid molecules according to the invention is not to be limited strictly to molecules comprising the sequences set forth as SEQ ID: 1 and 2. Rather the invention encompasses nucleic acid molecules carrying modifications like substitutions, small deletions, insertions or inversions, which nevertheless have substantially the biochemical activity of the $GABA_B$ receptor promoters 1a and/or 1b according to the invention. Included in the invention are consequently nucleic acid molecules, the nucleotide sequence of which is at least 95% homologous, preferably at least 96%, 97%, 98% or 99% homologous, with the nucleotide sequence shown as SEQ ID NO: 1 or 2 in the Sequence Listing.

The term "stringent hybridization conditions" is known in the art from standard protocols (e.g. Current Protocols in Molecular Biology, editors F. Ausubel et al., John Wiley and Sons, Inc. 1994) and could be understood as as stringent or more stringent than those defined by e.g. hybridization to filter-bound DNA in 0.5 M $NaHPO_4$, 7% sodium dodecyl sulfate (SDS), 1 mM EDTA at +65° C., and washing in 0.1×SSC/0.1% SDS at +68° C.

It will be appreciated that the nucleic acid sequences shown in the Sequence Listing is only an example within a large but definite group of nucleic acid sequences, which will have the $GABA_B$ receptor promoter activity.

In yet another aspect, the invention provides a vector transformed with a nucleic acid molecule of the present invention. The said vector can e.g. be a replicable expression vector, which carries a nucleic acid molecule according to the invention. In the present context the term "replicable" means that the vector is able to replicate in a given type of host cell into which is has been introduced. Examples of vectors are viruses such as bacteriophages, cosmids, plasmids and other recombination vectors. Nucleic acid molecules are inserted into vector genomes by methods well known in the art.

Another embodiment of the present invention is an expression system comprising nucleic acid molecules encoding $GABA_B$ receptor promoters P1a and/or P1b, or functionally equivalent modified forms, or active fragments thereof.

In preferred forms of this embodiment of the invention the said nucleic acid molecule is selected from: (a) a nucleic acid molecule comprising a nucleotide sequence set forth as SEQ ID NO: 1 and/or SEQ ID NO: 2; (b) a nucleic acid molecule comprising a nucleotide sequence capable of hybridizing, under stringent conditions, to a nucleotide sequence complementary to the polypeptide coding region of a DNA molecule as defined in (a).

In another preferred form of this embodiment of the invention the said nucleic acid molecule may be a nucleic acid molecule constituting a human $GABA_B$ receptor 1 promoter P1a, or a functionally equivalent modified form thereof, or active fragments thereof, in combination with a nucleic acid molecule constituting a human $GABA_B$ receptor 1 promoter P1b, or a functionally equivalent modified form thereof, or active fragments thereof.

In another preferred form of this embodiment of the invention the said nucleic acid molecule may be a nucleic acid molecule selected from:
(a) a nucleic acid molecule comprising a nucleotide sequence set forth as SEQ ID NO: 1;
(b) a nucleic acid molecule comprising a nucleotide sequence capable of hybridizing, under stringent conditions, to a nucleotide sequence complementary to the DNA molecule as defined in (a);

in combination with a nucleic acid molecule is selected from:
(a) a nucleic acid molecule comprising a nucleotide sequence set forth as SEQ ID NO: 2;
(b) a nucleic acid molecule comprising a nucleotide sequence capable of hybridizing, under stringent conditions, to a nucleotide sequence complementary to the DNA molecule as defined in (a).

The expression system may, in addition, comprise a reporter gene, the promoter and the reporter gene being positioned so that the expression of the reporter gene is regulated by the $GABA_B$ receptor 1 promoters P1a and/or P1b. Suitable expression systems according to the invention are e.g. bacterial or yeast plasmids, wide host range plasmids and vectors derived from combinations of plasmid and phage or virus DNA. Furthermore, an origin of replication and/or a dominant selection marker can be present in the vector according to the invention. Suitable reporter genes that can be used for the construction of expression systems according to the invention are e.g. the firefly luciferase gene, the bacterial chloramphenicol acetyl transferase (CAT) gene, the β-galactosidase (β-GAL) gene, and the green fluorescent protein (GFP) gene.

A further aspect of this embodiment of the invention is a host cell transfected with an expression system comprising nucleic acid molecules constituting $GABA_B$ receptor promoters P1a and/or P1b, or functionally equivalent modified forms thereof, or active fragments thereof.

Suitable host cells are cells known to express $GABA_B$ receptors or cells known to express transcription factors, which can influence the transcription of $GABA_B$ receptors. Host cells transfected with DNA encoding specific transcription factors can preferably be used to study the interaction with defined transcription factors and the $GABA_B$ receptor promoter.

Another embodiment of the invention is a method for the assay of $GABA_B$ receptor promoter activity said method comprising the use of a host cell transfected with an expression system comprising nucleic acid molecules constituting $GABA_B$ receptor promoters P1a and/or P1b, or functionally equivalent modified forms thereof, or active fragments thereof.

A further embodiment of the present invention is a method for the screening of compounds which are modulators of $GABA_B$ receptor 1 transcription, said method comprising the use of nucleic acid molecules constituting $GABA_B$ receptor P1a and/or P1b promoters.

Accordingly, the present invention provides a method for screening compounds which are modulators of $GABA_B$ receptor 1 transcription, comprising the steps of: (a) transfecting a cell host with a suitable expression system comprising a nucleic acid molecule constituting human $GABA_B$ receptor 1 promoter P1A, and/or a human $GABA_B$ receptor 1 promoter P1B or functionally equivalent modified forms, or active fragments thereof coupled to a reporter gene; (b) contacting a test compound with the cell; and (c) determining whether the test compound modulates the level of expression of the reporter gene.

In one aspect of this embodiment of the invention it is provided a method of screening of compounds which are modulators of $GABA_B$ receptor 1 transcription, wherein the cell host endogenously expresses $GABA_B$ receptor 1.

In another aspect of this embodiment of the invention it is provided a method of screening of compounds which are modulators of $GABA_B$ receptor 1 transcription, wherein the said cell host is further transfected with a suitable expression system comprising a nucleic acid molecule encoding one or more specific transcription factors. Preferably, the said transcription factors are selected from the group: CREB-1, CREB-2, CREM-1, ATF-1, ATF-2, ATF-3, ATF-4, Sp1, Sp2, Sp3, Sp4, AP-1, and AP-2.

A further embodiment of the invention is a transgenic non-human animal whose genome comprises an expression system comprising nucleic acid molecules constituting $GABA_B$ receptor promoters P1a and/or P1b, or functionally equivalent modified forms thereof, or active fragments thereof, coupled to a reporter gene.

Such transgenic non-human mammals can be generated by insertion of DNA comprising $GABA_B$ receptor promoters by microinjection, retroviral infection or other means well known to those skilled in the art, into appropriate fertilized embryos to produce a transgenic animal (Hogan B. et al Manipulating the Mouse Embryo, A Laboratory Manual, Cold Spring Harbor Laboratory (1986)).

Accordingly, the present invention provides a method for the screening of compounds which are modulators of $GABA_B$ receptor 1 transcription, comprising the use of a transgenic non-human animal whose genome comprises an expression system comprising nucleic acid molecules constituting $GABA_B$ receptor promoters P1a and/or P1b, or functionally equivalent modified forms thereof, or active fragments thereof, coupled to a reporter gene, or tissues or cells isolated from such transgenic animals.

EXAMPLES

The following examples are preferred non-limiting examples embodying preferred aspects of the invention.

Example 1

Isolation and Identification of Human $GABA_BR1$ Promoters P1a and P1b

Genomic DNA containing the human $GABA_B$ receptor gene was isolated from human genomic libraries and genomic DNA. Human genomic libraries were obtained from Clontech (Palo Alto, Calif., USA). The libraries were constructed from female leukocyte DNA (catalogue # HL1111J), cloned into λEMBL-3 vector. The average size of inserts are 16 kb and the number of independent clones are $1.7 \times 10^6$. Human genomic DNA was obtained from Clontech (catalogue # 6550-1). In order to isolate recombinant phases containing exon and intron sequences of the human $GABA_B$ receptor gene, 48 individual bacterial plates with a diameter of 150 mm and approximately $4 \times 10^4$ individual plaques per plate, were screened. The methods and solutions used were as described in the Library Protocol Handbook: General Procedures for the Hybridization of Lambda Phage Libraries w/DNA Probes (Clontech) with some modifications as will be apparent from the following.

The experiment was carried out essentially as follows. The numbers are given per plate basis. A sample of the phage library diluted in 0.1 ml sterile lambda diluent was prepared in order to obtain an estimated titer of 40,000 pfu (plaque forming units). A 0.6 ml LB-medium culture of the *E. coli* host strain K802 (obtained from Clontech) was infected with 40000 pfu recombinant phages for 15 minutes at 37° C. The culture was then mixed with 7 ml top agarose (6.5 g of agarose added per liter LB) and poured onto LB plates. The plates were incubated at 37° C. for approximately 7 hours. The plates were then chilled at +4° C.

Plaque hybridization experiments were as follows. Membrane filters, Colony/Plaque Screen (DuPont, Wilmington, Del., USA), were placed onto the top of the plates for 3 minutes. For denaturation of DNA the filters were removed and floated in 0.5 M NaOH on a plastic wrap for 2 minutes, with the plaque side up. This step was repeated once to ensure efficient denaturation. Following neutralization the membrane filters were placed in 1M Tris-HCl pH 7.5, two times 2 minutes and allowed to dry.

To obtain probes for DNA hybridization screening of the membrane filters, a $GABA_B$ receptor cDNA clone was digested with SacII and a 479 bp fragment, separated by agarose electrophoresis, excised and transferred to a polypropylene microcentrifuge tube. Additional probes were obtained by PCR amplification of various regions of the $GABA_B$ receptor cDNA. The isolated cDNA fragment was $^{32}$P-labeled using Megaprime DNA labeling system (Amersham Pharmacia Biotech, Uppsala, Sweden) by the following procedure. Water was added at a ratio of 3 ml per gram of gel, and placed in a boiling water bath for 7 minutes to melt the gel and denature the DNA. A volume of DNA/agarose solution containing 25 ng of DNA was added to the labeling reaction, according to the supplier's instructions. Labeled nucleotides were removed from DNA labeling reactions using MicroSpin™ G-50 Columns (Amersham Pharmacia Biotech, Uppsala, Sweden).

The DNA hybridization reaction was performed under stringent conditions according to the method described below. The filter membranes were prehybridized at 65° C. for at least 1 hour in a solution composed of 1% SDS, 1M NaCl, and 10% dextran sulfate using a hybridization oven (Hybaid Ltd, Ashford, UK). Following prehybridization a solution containing denatured herring sperm DNA of a final concentration of 100 μg/ml and the $^{32}$P-labeled DNA probe at a concentration <10 ng/ml (for optimal signal to background ratio) was added to the prehybridization solution and the membrane filters were incubated at 65° C. for 10-20 hours. Following the removal of the hybridization solution the membrane filters were first washed in a 2×SSC (0.3M NaCl, 0.03M Na-citrate), 1% SDS solution two times for 5 minutes at room temperature. In the next step, the membrane filters were incubated at 60° C. two times for 30 minutes each in the same solution. In a third step, the filters were washed two times at room temperature in 0.1×SSC. Finally, the membrane filters were placed on a sheet of filter paper with the DNA face up, and allowed to dry. The dried membrane filters were then exposed to X-ray films and autoradiographed.

Of the approximately $2×10^6$ individual plaques analyzed, four hybridizing plaques were detected and isolated. These four isolates were designated #GR1, #GR12, #GR13 and #GR41, respectively. After several rescreening experiments, the recombinant phage DNA was purified using Qiagen Lambda Midi Kit (Qiagen GmbH, Germany). The purified DNA was digested with SalI and the fragments representing the inserts were isolated by agarose electrophoresis.

The 16 kb insert of isolate #GR 13 was cloned into SalI digested linearized pUC19, resulting in the plasmid pAM364. The insert was analyzed by PCR, restriction mapping and hybridization to $^{32}$P-labeled DNA fragments representing various regions of the $GABA_B$ receptor cDNA.

The cloned fragment in the plasmid pAM364 was characterized by restriction enzyme mapping, using EcoRI, HindIII, PstI, and BamHI. The approximate positions of the exons and the approximate size of the introns were analyzed and determined by PCR-based exon-exon linking and agarose gel electrophoresis.

In order to facilitate nucleotide sequence analysis, 7 restriction sub-fragments derived from pAM364 were isolated and cloned individually into pUC19. The following strategy was employed; by combining PCR primers located within the pUC19 sequence either upstream or downstream of the cloning site, with a PCR primer with defined orientation and specific for the $GABA_B$ receptor derived subcloned fragment allowed the sequence determination.

The inserts were subjected to nucleotide sequence analysis. The nucleotide sequences for all subclones were determined using a Thermo Sequenase dye terminator cycle sequencing pre-mix kit (Amersham Pharmacia Biotech, Uppsala, Sweden). As primers for sequencing reactions specific oligonucleotides complementary to pUC19 or primers complementary to the human $GABA_B$ receptor cDNA were used.

The sequence of the human $GABA_B$ receptor gene fragment cloned in the plasmid pAM364 has previously been revealed (see PCT/SE98/01947). This genomic fragment was shown to contain the complete exons 1-11 and the complete introns 1-10 of the human $GABA_B$ receptor gene as well as >3 kb sequence upstream of exon 1. The elucidation of the gene organization revealed that the human $GABA_BR1a$ and $GABA_BR1b$ are splice variants encoded by a single gene.

In order to localize the putative human $GABA_B$ receptor promoter, we investigated the genomic sequence for the presence of consensus sequences of known regulatory promoter elements. To our surprise, we found that promoter elements, clustered in two regions: one region upstream of exon 1, and the other region in intron 5, just upstream of exon 6. We concluded that the human $GABA_B$ receptor may be regulated by two independent promoters, and not by one single promoter as expected. The first putative promoter, denoted P1a (SEQ ID NO:1) and described in detail below, may regulate transcription of $GABA_BR1a$-type splice variants and the second putative promoter, denoted P1b (SEQ ID NO: 2) and described in detail below, may regulate transcription of $GABA_BR1b$-type splice variants.

As indicated in the schematic representation of P1a and P1b (FIG. 2), both putative promoters lack a TATA box. However P1b has an initiator (Inr) element in position 4375-4381 which is located 24-30 bp upstream of the position corresponding to the 5' end of the longest known cDNA isolated with "rapid amplification of cDNA ends" (RACE) PCR amplification. The Inr element may therefore direct the start of transcription from P1b. P1a contains neither a TATA or an Inr element and the transcription from R1a may therefore initiate from different start sites which is often the case in promoters lacking TATA boxes or Inr elements. Both P1a and P1b contain multiple GC rich regions at pos. 3009-3016, 3037-3044 and 3116-3123 in R1a and pos. 4080-4087, 4196-4204, 4241-4249 and 4272-4279 in R1b, which are potential binding site for the SP1 family of transcription factors. SP1 binding sites are often found in TATA lacking promoters where they often substantially contribute to transcription. In addition, to the indicated GC sequences in FIG. 2 there are also other GC motifs that may function as SP1 binding sites. P1a further contains an activator protein-1 (AP-1) site at position 1497-1503. AP-1 sites are recognized by AP-1 transcription factors which consists of homodimers of members of the Jun family or Fos/Jun heterodimeric complexes. AP-1 complexes also interact, by protein-protein interactions, with members of the steroid receptor family and are therefore also targets for steroid receptor signaling. In addition to the GC motifs P1b also contain an activator protein-2 (AP-2) site at position 3844-3851 and a cAMP responsive element (CRE) at position 4308-4315. Especially the finding of a consensus CRE (TGACGTCA) is interesting as this promoter element is found in many genes regulated by cAMP which are bound and regulated by members of the ATF/CREB gene family. This sequence may therefore be an important target for cAMP mediated signaling via G-protein coupled receptors, including $GABA_B$ receptors.

We conclude that transcription of the human $GABA_B$ receptor gene may be regulated by two putative promoters, P1a and P1b, that may independently regulate expression of human $GABA_B$ receptor 1a and 1b splice isoforms, respectively.

Example 2

Determination of $GABA_BR1$ Promoter P1a and P1b Activity

To experimentally determine if P1a and P1b indeed act as promoters, we fused these regions to a cDNA encoding firefly luciferase to be used as a reporter of promoter activity in transfected cells.

Reporter constructs containing R1a and R1b promoter fragments were generated by PCR using plasmid pAM 364, containing genomic sequence covering the promoter regions, as template. PCR reaction was performed by standard procedure (Perkin Elmer). Briefly, an initial denaturation at 95° C. for 4 min was followed by 35 cycles of denaturation at 95° C. for 1 min, annealing at 60° C. for 1 min, elongation at 72° C. for 1 min and finally a 7 min elongation at 72° C. In the sequence for primers used to generate promoter fragments (for details see Table 1. below), a Nhe I and Hind III endonuclease restriction enzyme site was introduced, in 5' and 3' primers respectively, to enable sub-cloning into Nhe I/Hind III digested pGL3-Basic luciferase reporter vector (Promega). Hence, complete promoter-reporter constructs (pAM440, pAM438 and pAM436) contain R1a and R1b promoter fragments (indicated size see table) fused to the luciferase reporter gene. Plasmid DNA were purified using Qiagen tip-100 columns according to suppliers instruction. Correct fragment insertion was verified by DNA sequencing.

TABLE 1

Nucleotide sequence of primers used to generate promoter fragments

| Primer No. | Restriction site | Promoter sequence | Position | Sequence 5'-3' |
|---|---|---|---|---|
| 1582 | HindIII (AAG CTT) | SEQ ID NO: 1 | 3440-3424 | AAG CTT CTC GGC GCG CGG GCC CG (SEQ ID NO: 3) |
| 1583 | NheI (GCT AGC) | SEQ ID NO: 1 | 2341-2362 | GCT AGC CAA GAG CTT CTG GAG CCG (SEQ ID NO: 4) |
| 1584 | NheI (GCT AGC) | SEQ ID NO: 1 | 720-741 | GCT AGC TGT TAC ATG CAG AGC AAT C (SEQ ID NO: 5) |
| 1585 | HindIII (AAG CTT) | SEQ ID NO: 2 | 4439-4421 | AAG CTT CCT ACG GCC CCC GCG (SEQ ID NO: 6) |
| 1586 | NheI (GCT AGC) | SEQ ID NO: 2 | 3321-3340 | GCT AGC GCG CAC TGC AAT GCC CTC (SEQ ID NO: 7) |

To determine putative promoter activity, the reporter gene constructs were introduced into mammalian cells by transfection. In this study the cell line ND7/23 (ECACC Ref No: 92090903) was used. ND7/23 is a hybrid cell line originating from a mouse neuroblastoma (N18tg2) fused by PEG to a rat dorsal root ganglion neuron cell line. This cell line was chosen since it express functional $GABA_B$ receptors as evidenced by radioligand binding studies. Cells were cultured in a 1:1 mixture of Dulbecco's modified medium (DMEM) and Ham's F12 medium supplemented with 10% (v/v) fetal bovine serum (FBS). Cells were grown at 37° C. in an atmosphere of 5% $CO_2$. ND7/23 cells ($4\times10^5$) were transfected using the DMRIE-C reagent according to manufacturer's protocol (Gibco). Briefly, cells were seeded in 6 well tissue culture plates (Nunc) the day before transfection. Next day, 2 μg of promoter-reporter construct and 1 μg of transfection control construct (pSV-β-Galactosidase, Promega) was mixed with 0.5 ml Optimem media (Gibco). DNA containing media was then mixed with an equal volume (0.5 ml) of Optimem containing 4 μl of DMRIE-C reagent and the combined mixture was then incubated for 45 min. After incubation, the transfection mixture was added to the cells, which were washed with Optimem media just prior to addition of transfection mixture. Following 5 h incubation at 37° C., an equal volume of 1:1 mixture of Dulbecco's modified medium (DMEM) and Ham's F12 medium supplemented with 20% (v/v) fetal bovine serum (FBS) was added to the cells. Cells were incubated for 24 h at 37° C. with or without cAMP enhancing supplement as indicated in FIG. 3. Before cell harvest, cells were washed in PBS (7.6 mM $Na_2HPO_4/NaH_2PO_4$ pH 7.4 and 120 mM NaCl), then cell extracts were prepared by addition of 250 μl reporter lysis buffer (Promega) to cells, followed by transfer of cell suspension to 1.5 ml tubes. Cells were further lysed by one round of freeze-thawing and 15 s of vortex. Cell debris were removed by 2 minutes of centrifugation at 12 000 g. Luciferase activity in cell extracts was measured in a Luciferase Assay System (Promega), where 40 μl of cell extracts was added to a 96-well plate (Maxisorp, Nunc) and mixed with 50 μl of luciferase substrate. Luciferase activity was then measured in a LUMIstar (BMG Lab technologies). As internal control for transfection efficiency, β-Galactosidase (β-Gal.) activity was measured in 96-well plate (Maxisorp, Nunc) using a β-Galactosidase Enzyme Assay (Promega) according to suppliers protocol. As seen in FIG. 3, transient transfection of ND7/23 cells shows that both P1a and P1b has promoter activity as pAM438, pAM436 and pAM440 (FIG. 3) result in reporter expression, while the pAM442 (vector control) has very low activity. In addition, this experiment demonstrates that especially reporter expression originating from pAM440 (R1b) can be induced by the cAMP activating agent forskolin. Moreover, forskolin induced expression may also be further enhanced in the presence of the phosphodiesterase inhibitor 1-methyl-3-isobutylxanthine (IBMX) although this experiment does not show a significant difference.

In conclusion, this experiment demonstrate that P1a and P1b both have promoter activity and that the degree of activity can be modulated using the cAMP activating agent forskoline.

Example 3

Screening for Substances Modulating P1a and P1b Activity

Modulating $GABA_B R1$ expression in a controlled way is a means to regulate signaling through $GABA_B$ receptors which could be of significant therapeutic value for a variety of conditions. Particularly, the ability to specifically regulate expression of either 1a- or 1b-type $GABA_B$ receptor splice isoforms could be of medical value if these isoforms could be attributed to specific conditions.

The experiment presented in Example 2 demonstrates that the use of P1a and P1b promoter/reporter constructions can be used to monitor $GABA_B R1$ expression in screens for therapeutic agents that can modify the expression of $GABA_B$ receptor 1 isoforms. A screen for P1a and P1b modulating substances could be performed in ND7/23 cells as described in Example 2. A screen for P1a and P1b modulating substances could in addition be performed in any cell type with endogenous expression of $GABA_B$ receptor 1 and 2 isoforms, in cells expressing recombinant $GABA_B$ receptor 1 and 2 isoforms and in intact cells and in extract or fractions of cells expressing endogenous and recombinant proteins modulating $GABA_B$ receptor function. Such screens could furthermore be done in tissues and in living organisms.

Example 4

Functional Analysis of $GABA_B$-R1 Promoter Fragments and Modified Forms

In order to identify functionally active promoter fragments of P1a and P1b a deletion analysis of DNA fragments containing promoter fragments can be performed in two steps.

It is anticipated that P1a and P1b comprise active fragments that can mediate increased expression by binding of transcription factors that are activators as well as active fragments which can mediate decreased expression by binding of transcription factors that are repressors.

In the first step, promoter fragments mediating expression of a reporter gene when used in reporter constructs can be stepwise deleted or truncated to identify important regions. Briefly, truncated or deleted promoter fragments are created by PCR using specific primers and the already identified promoter sequences as template. Reporter constructs (as exemplified in this application) comprising the deleted or truncated promoter fragments are then created. These reporter constructs can then be used in transfection experiments, as described above, to identify important regions of the promoters manifested in altered expression from constructs lacking active fragments compared to none-deleted constructs.

In the second step, the exact location and sequence of transcription factor binding sites within active fragments can be determined by PCR technique using specific primers harbouring desired mutations. Such promoter fragments, with specifically mutated promoter regions, can be used in transfection experiments, similar to those described above, to determine the exact sequence of functionally important nuclear factor binding sites within active promoter fragments, manifested in altered expression from constructs with mutated DNA sequence compared to none-mutated control constructs with equal size.

The above mentioned strategy can also be used to identify the specific active promoter fragments which are important for the effect on promoter activity of active substances identified when screening for therapeutic agents regulating $GABA_B$-R1 expression.

Example 5

Activity of $GABA_B R1$ Promoter P1a and P1b Fragments

Reporter constructs containing P1a and P1b promoter fragments were generated by PCR as described in Example 2 and fused to the firefly luciferase reporter gene. The generated constructs are visualised in FIG. 4.

Putative transcription initiation sites were identified at position 3207 in SEQ ID NO:1 for P1a and at position 4405 in SEQ ID NO:2 for P1b. The positions in the promoter region shown in FIG. 4 were calculated setting the transcription initiation sites as position +1.

The generated promoter reporter constructs (see FIG. 4) were used to transfect ND7/23 cells. As shown in FIG. 4, deletion of P1a promoter region in between position −2549 bp and −361 caused an increase in expression, indicating putative repressor regions between position −2549 and −361. Moreover, when 175 bp of the 5' untranslated region were removed (compare the third and fourth P1a constructs from the top) there was no detected difference in promoter activity and constructs with the shorter P1a 5'-untranslated region were therefore used for mutational analysis throughout the rest of the study. Additional deletions of the P1a promoter from position −361 to −46 caused a stepwise decrease of the expression that seem to correlate with removal of promoter regions containing GC elements (I-III). This indicate that 361 bp of the P1a promoter can confer optimal expression and that promoter elements essential for R1a-type expression, including GC elements I-III are located between position −361 and −46. Similar to the P1a promoter, deletion of P1b promoter region from position −3238 bp to −390 caused an increase in expression, indicating putative repressor regions between −1084 and −390. Also, additional deletions of the P1b promoter from position −390 to −88 caused a stepwise decrease of the expression that correlate with removal of promoter region GC elements (IV-VII) as well as the consensus CRE. Although there was still some promoter activity left when the P1b promoter region was deleted down to position −88, the major promoter elements essential for R1b-type expression seem to be located between position −390 and −88. Comparison of P1a and P1b expression also indicates that, P1b mediated expression was higher (approximately 3-4 fold) than for P1a.

Example 6

Mutational Analysis of P1a and P1b Promoter Element Function

As shown in FIG. 4, reporter constructs −361 in P1a (short 5'UTR) and −390 in P1b conferred optimal expression of the respective promoters. In order to determine the importance of the promoter elements that was found within these regions, P1a (−361) and P1b (−390) constructs were used as templates to obtain reporter constructs with promoter regions mutated at specific sites. For the mutated promoter constructs, a 3 bp substitution was introduced by "quick change" site directed mutagenesis.

Site-directed mutagenesis: Mutant constructs were prepared with a QuickChange site-directed mutagenesis kit (Strategene, La Jolla, Calif.) according to the manufacturer's instructions. The mutagenic oligonucleotide primers are listed in Table 2. All constructs were verified by DNA sequencing.

TABLE 2

Oligonucleotide primers used in the mutagenesis experiments

| Primer | | | Primer Sequences |
|---|---|---|---|
| 1949 P | R1b | Cre Fwd | CGCCGCCCGTTTGGTCAGAGCCCCT (SEQ ID NO: 8) |
| 1950 P | R1b | Cre Rev | AGGGGGCTCTGACCAAACGGGCGGCG (SEQ ID NO: 9) |
| 1951 P | R1a | GCI Fwd | CTCTCTTCCCCCCTAACTGCCTTCCC (SEQ ID NO: 10) |
| 1952 P | R1a | GCI Rev | GGGAAGGCAGTTAGGGGGAAGAGAG (SEQ ID NO: 11) |
| 1953 P | R1a | GCII Fwd | GGCGGTCCAGTTAGGGGCTGGGATCC (SEQ ID NO: 12) |
| 1954 P | R1a | GCII Rev | GGATCCCAGCCCCTAACTGGACCGCC (SEQ ID NO: 13) |
| 2051 P | R1a | GCIII Fwd | CCTCTCCACCGCCCTAACCACCGCGCTGTG (SEQ ID NO: 14) |
| 2052 P | R1a | GCIII Rev | CACAGCGCGGTGGTTAGGGCGGTGGAGAGG (SEQ ID NO: 15) |
| 2053 P | R1b | GCIVs Fwd | CCCCAGCTCCCGCCCTAACCCCCACCCC (SEQ ID NO: 16) |
| 2054 P | R1b | GCIVs Rev | GGGGTGGGGGTTAGGGCGGGAGCTGGGG (SEQ ID NO: 17) |
| 2055 P | R1b | GCV Fwd | CGCTTCCCTCCCCTAACCCTTCCTGCC (SEQ ID NO: 18) |
| 2056 P | R1b | GCV Rev | GGCAGGAAGGGTTAGGGGAGGGAAGCG (SEQ ID NO: 19) |
| 2057 P | R1b | GCVI Fwd | CCCTCCCCTCCCCTAACCTCCGACTGT (SEQ ID NO: 20) |
| 2058 P | R1b | GCVI Rev | ACAGTCGGAGGTTAGGGGAGGGGAGGG (SEQ ID NO: 21) |
| 2059 P | R1b | GCVII Fwd | CTCCGCCCACCCCTAACTCCTGGCAC (SEQ ID NO: 22) |
| 2060 P | R1b | GCVII Rev | GTGCCAGGAGTTAGGCGTGGGCGGAG (SEQ ID NO: 23) |
| 2146 P | R1b | GCIVd Fwd | CCCCAGCTCCCTAACTAACCCCCACCCC (SEQ ID NO: 24) |
| 2147 P | R1b | GCIVd Rev | GGGGTGGGGGTTAGTTAGGGAGCTGGGG (SEQ ID NO: 25) |

Bases that are labelled bold correspond to designed mutations

Obtained promoter constructs were then used to transfect ND7/23 cells. As shown in FIG. 5, single point mutations of GC elements I, II and III reduced P1a expression to approximately 65-75% compared to wild-type, while double-mutations (I/II, I/III and II/III, respectively) resulted in a further decrease to approximately 55-60% of wild-type expression levels. When all three GC elements (I-III) were mutated, the reporter expression was reduced to approximately one third (33%) of wild-type expression. Together, these results suggest that the three GC-elements found in P1a, all contribute to P1a mediated expression in a substantial and additive manner. However, the fact that one third of the P1a promoter activity still remains suggests that there are additional promoter elements within P1a contributing to P1a mediated expression.

In contrast to P1a, single mutations of the four P1b GC elements (IV, V, VI and VII) only caused small reductions of expression to approximately 75-90% compared to wild-type. The relatively modest contribution by the four P1b GC elements was also demonstrated by a promoter construct were all four GC elements (IV-VII) had been mutated. This construct retained 63% of P1b expression compared to the wild-type construct. However, when the P1b CRE consensus site was mutated (CRE), a dramatic reduction of P1b mediated expression (approximately 50%) was obtained. Moreover, when the CRE mutation was combined with mutations of each GC element respectively, a further reduction was observed. Most notably, the promoter construct containing a double mutation of the CRE and GC V (CRE/V) promoter elements resulted in a substantial reduction of P1b expression to approximately 26%, similar to the construct where all five P1b promoter elements were mutated (CRE/IV-VII) where 24% of the expression still remained compared to wild-type. Together these data demonstrates the absolute importance of the consensus CRE site for P1b expression, alone or in combination with the GC elements (IV, V, VI and VII), of which GC element V seems to contribute most. The fact that one fourth of P1b promoter activity still remains suggests that, as for P1a, there are additional promoter elements within P1b that may contribute to P1b mediated expression.

Example 7

Identification of Factors Interacting with the P1b CRE Site

Electrophoretic Mobility Shift Assays (EMSA)

Electrophoretic mobility shift assays (EMSA) can be used to identify nuclear factors that interact with P1a and P1b promoter elements. In an attempt to identify factors interacting with the P1b CRE site, we performed gelshift analysis with super-shift antibodies that recognise members of the CREB/ATF family of transcription factors. The DNA-binding reactions (12 µl) were done as follows; 2-3 fmol $^{32}$P-labeled double-stranded oligonucleotide corresponding to the P1b CRE site was mixed with 5 µg crude nuclear extracts from ND7/23 cells and 1 µg poly (dI-dC), 25 mM Hepes (pH 7,9), 150 mM KCl, 5 mM dithiothreitol and 10% glycerol (Schneider et al 1986, Nucleic Acids Research. 14:1303-17). In the supershift lane (FIG. 6) the ATF-1 p35/CREB-1 p43/CREM-1 reactive antibody (sc-270 from Santa Cruz Biotechnology, Santa Cruz, Calif.), was pre-incubated at room temperature for 20 min before addition of $^{32}$P-labeled probe. After incubation at room temperature for 15 min, protein-DNA complexes were resolved on precasted DNA-retard gels (Novex™) containing 6% polyacrylamide prepared with 0.5×TBE as gel buffer. Following electrophoresis, gels were dried and visualised by autoradiography.

As shown in FIG. 6, addition of a monoclonal CREB/ATF supershift antibody (reactive with members of the ATF/CREB family such as ATF-1 p35, CREB-1 p43 and CREM-1 of mouse, rat and human origin) into the EMSA reaction mixture results in a distinct shift of the nuclear factor(s) that interacts with the P1b CRE site, while no super-shift was observed when the same antibody was added to other EMSA reactions containing other promoter elements (data not shown). This data suggests that the complex formed with the P1b CRE site contains a member of the CREB/ATF family.

Similar further studies can be performed in order to determine which factor(s) that interact with the various promoter elements in P1a and P1b.

Example 8

Use of Recombinant Transcription Factors in the Study of P1a and P1b Promoter Activities Cells with stably integrated or with transiently transfected P1a/P1b reporter constructs can be transfected with cDNA encoding specific transcription factors to make reporter cells suitable for investigations of P1a and P1b activities mediated by said transcription factors. Reporter cells can alternatively be generated by delivery of transcription factors into similar cells by various means such as e.g. microinjection and lipofection. Reporter cells can be utilised for screening of compounds, which are modulators of $GABA_B$ receptor 1 transcription.

The figure shows the organization of the human $GABA_B$ receptor gene. Exons, represented by vertical squares/bars, are numbered (1-23). Translational start and stop sites are indicated by arrows. Location of human $GABA_B$ receptor 1 promoters P1a (SEQ ID NO: 1) and P1b (SEQ ID NO: 2) are indicated. The extent of human $GABA_B$ receptor genomic sequence cloned in plasmid pAM 364 is indicated by a horizontal bar.

Figure 1:
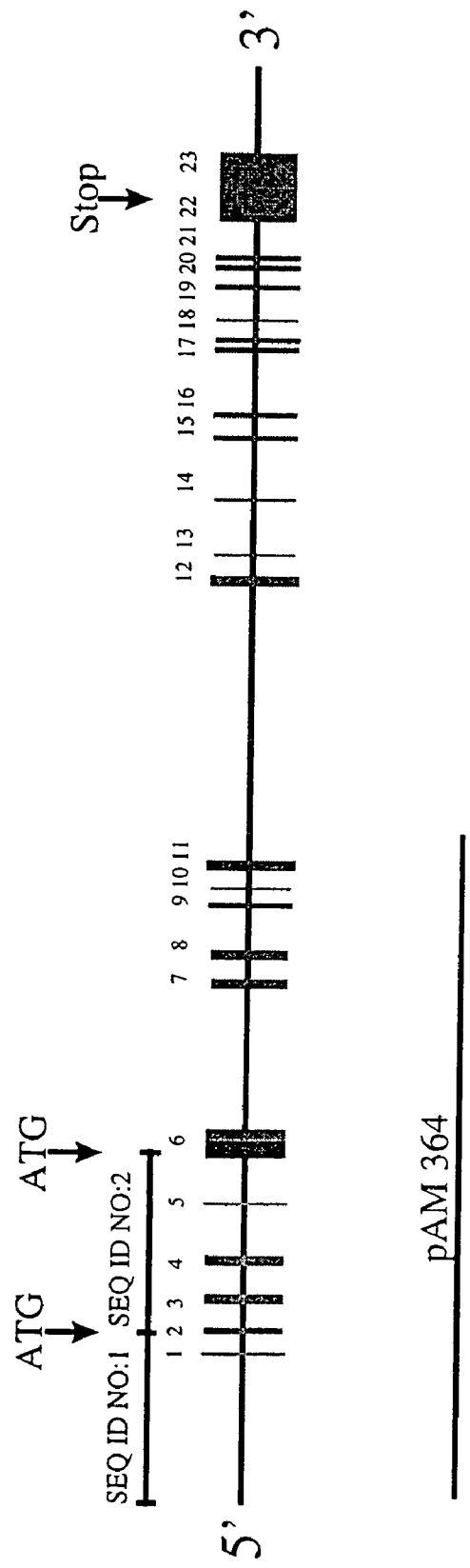
FIG. 1. The human $GABA_B$ receptor gene
Figure 2:
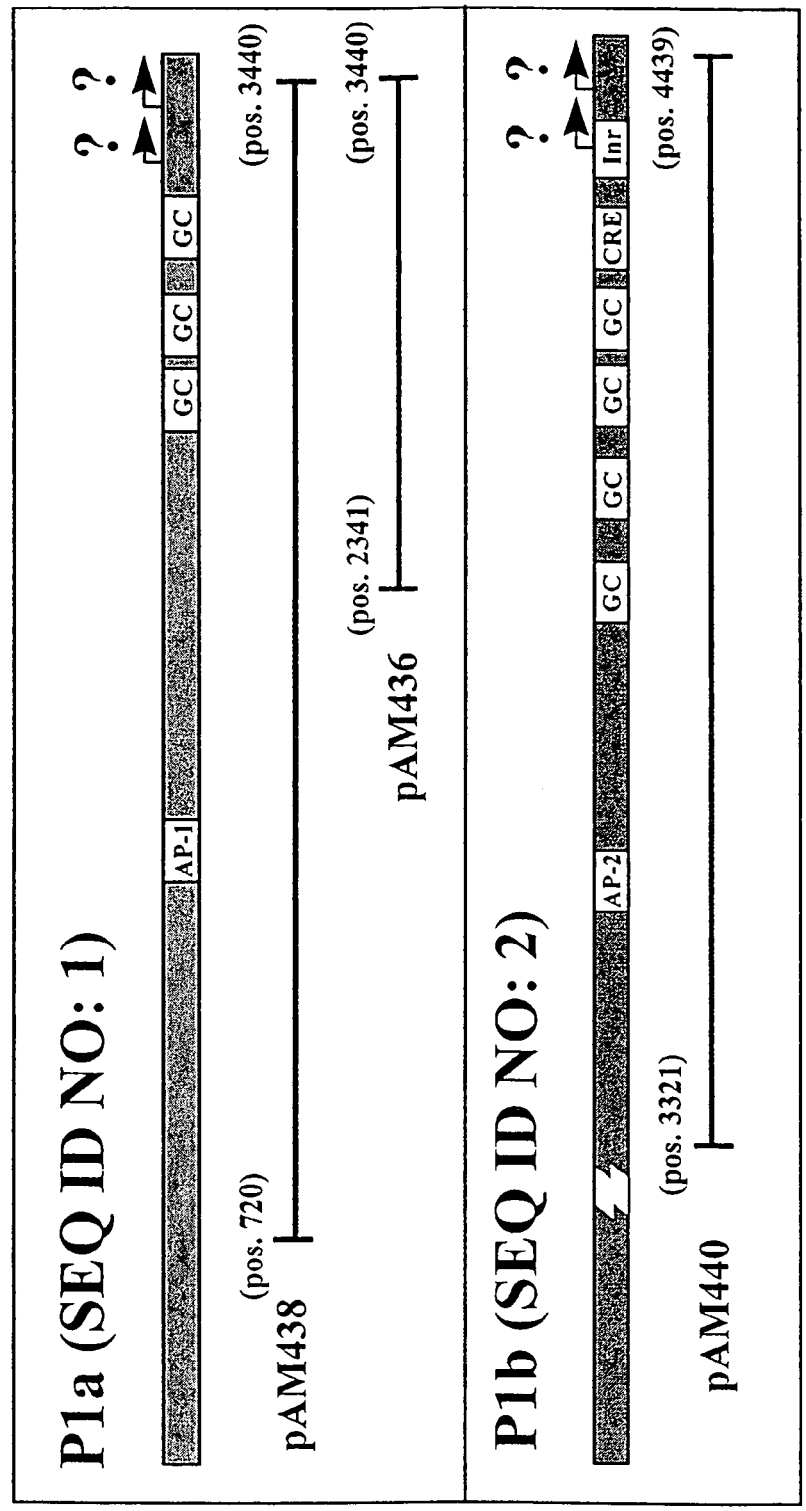

FIG. 2. Schematic representation of the P1a and P1b promoters

DNA fragments used to generate reporter constructs, corresponding to the positions in the P1a and P1b promoter sequence, are shown below each promoter. Putative promoter elements in each promoter are indicated. Arrows indicate putative positions for start of transcription.

Figure 3:
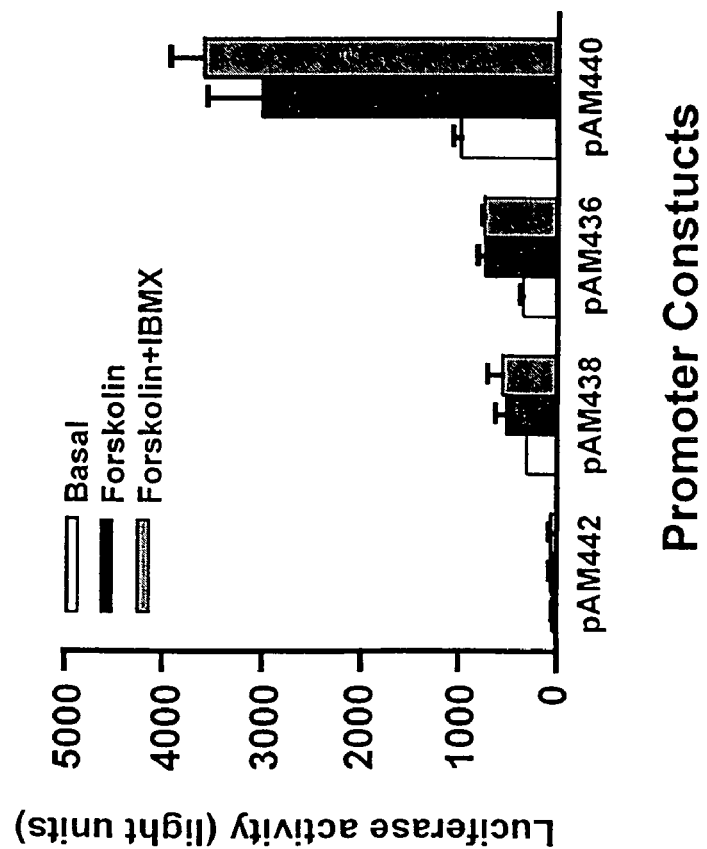

FIG. 3. Determination of $GABA_B$ receptor 1 promoter P1a and P1b activity

ND7/23 cells ($4 \times 10^5$) were transfected with promoter-luciferase constructs as described above. After transfection, cells were cultured in media without supplement (basal) or in the presence of Forskolin (10 μM) or Forskolin (10 μM)+1-methyl-3-isobutylxanthine (0.125 mM) for 24 h. After incubation, cells were harvested and luciferase activity measured. Luciferase activity, minus background, is shown as arbitrary light units measured in 40 μl of cell extracts. Relative values represent the mean±SEM of two individual experiments.

Figure 4:
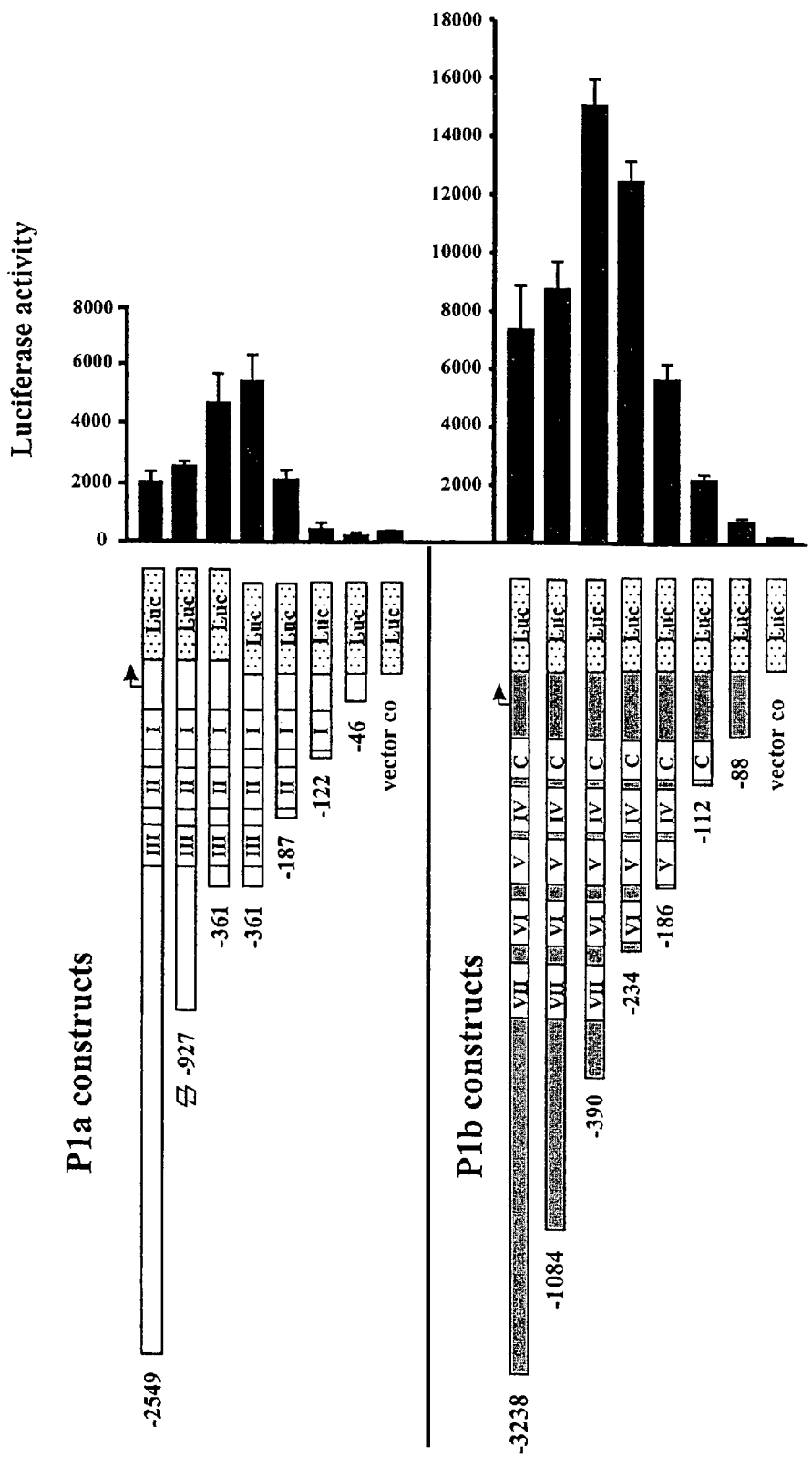

FIG. 4: Deletion analysis of the GBR1 promoters in ND7/23 cells

ND7/23 cells ($4 \times 10^5$) were transfected with P1a and P1b promoter-luciferase constructs as outlined above. After transfection, cells were cultured for 24 h, harvested and luciferase activity was measured. Luciferase activity, minus background, is shown as arbitrary light units measured in 10 μl of cell extracts. Relative values represent the mean±SEM of duplicate samples from at least three individual experiments.

Figure 5:
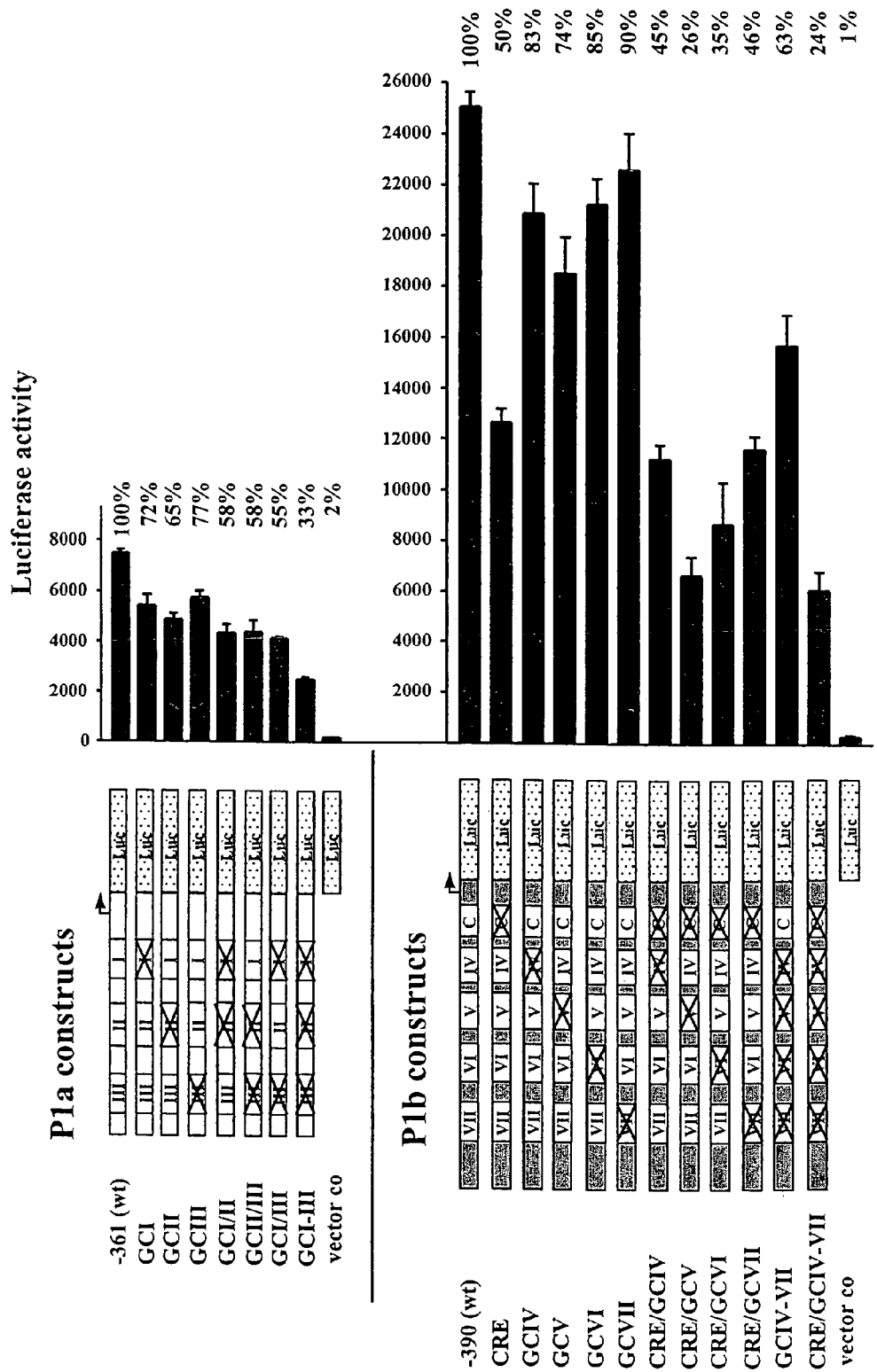

FIG. 5. Effect of P1a and P1b promoter element mutations on promoter activities.

ND7/23 cells ($4 \times 10^5$) were transfected with wild-type and mutated P1a and P1b promoter-luciferase constructs as described above. The point mutations in the promoter constructs are outlined to the left. After transfection, the cells were cultured for 24 h. After incubation, cells were harvested and luciferase activity measured. Luciferase activity, minus background, is shown as arbitrary light units measured in 10 μl of cell extracts. Relative values represent the mean±SEM of duplicate samples from at least three individual experiments. Relative expression level of mutated constructs are indicated to the left with the P1a and P1b "wild-type" expression level set as 100%.

Figure 6:
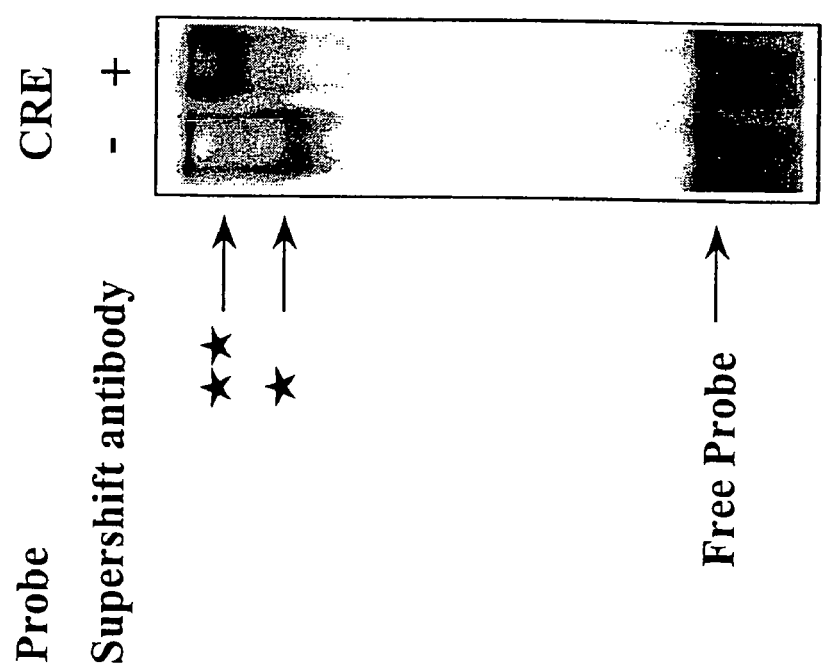

FIG. 6. Identification of nuclear factors binding to the P1b consensus CRE site using CREB/ATF super-shift antibodies.

Nuclear extracts (5 μg) from ND7/23 cells were incubated with double-stranded $^{32}$P-labeled oligonucleotides containing the P1b consensus CRE site (sense:5'-CGCCGCCCGT-GACGTCAGAGCCCCCT-3' (SEQ ID NO: 26)). In lane 1, no antibody was added. In lane 2, a mouse monoclonal antibody (sc-270 Santa Cruz Biotechnology, Santa Cruz, Calif.) reactive with members of the ATF/CREB family such as ATF-1 p35, CREB-1 p43 and CREM-1 was pre-incubated at room temperature for 20 mm before addition of $^{32}$P-labeled probe. The specific complex between nuclear factors and the CRE is indicated by a star and the super-shifted complex is indicated by two stars.

The invention claimed is:

1. An isolated nucleic acid molecule constituting a human GABA$_B$ receptor 1 promoter P1a set forth as SEQ ID NO: 1, or a functionally equivalent modified form thereof, or an active fragment thereof, wherein said modified form or active fraqment is at least 95% homologous to said isolated molecule.

2. The nucleic acid molecule according to claim 1 selected from the group consisting of:
   (a) a nucleic acid molecule comprising a nucleotide sequence set forth as SEQ ID NO: 1; and
   (b) a nucleic acid molecule comprising a nucleotide sequence capable of hybridizing to a filter-bound nucleotide sequence complementary to the polypeptide codinq region of a DNA molecule as defined in (a) in 0.5 M NaHPO$_4$, 7% sodium dodecyl sulfate (SDS), 1 mM EDTA at 65° C., with washing in 0.1×SSC/0.1% SDS at 68° C.

3. An isolated nucleic acid molecule constituting a human GABA$_B$ receptor 1 promoter P1b set forth as SEQ ID NO: 2, or a functionally equivalent modified form thereof, or an active fragment thereof, wherein said modified form or active fragment is at least 95% homologous to said isolated molecule.

4. The nucleic acid molecule according to claim 3 selected from the group consisting of:
   (a) a nucleic acid molecule comprising a nucleotide sequence set forth as SEQ ID NO: 2; and
   (b) a nucleic acid molecule comprising a nucleotide sequence capable of hybridizing to a filter-bound nucleotide sequence complementary to the polypeptide coding region of a DNA molecule as defined in (a) in 0.5 M NaHPO$_4$, 7% sodium dodecyl sulfate (SDS), 1 mM EDTA at 65° C., with washing in 0.1×SSC/0.1% SDS at 68° C.

5. A nucleic acid molecule comprising a nucleic acid molecule according to claim 1, in combination with a nucleic acid molecule according to claim 3.

6. A nucleic acid molecule comprising a nucleic acid molecule according to claim 2, in combination with a nucleic acid molecule accordinq to claim 4.

7. A vector comprising a nucleic acid molecule according to any one of claims 1 to 4.

8. An isolated cultured cell host comprising a vector according to claim 7.

9. An isolated expression system comprising a nucleic acid molecule constituting a human GABA$_B$ receptor 1 promoter P1a set forth as SEQ ID NO: 1, or a functionally equivalent modified form thereof, or an active fragment thereof, wherein said modified form or active fragment is at least 95% homologous to said isolated molecule.

10. An expression system according to claim 9, comprising a nucleic acid molecule selected from the group consisting of:
    (a) a nucleicacid molecule comprising a nucleotide sequence set forth as SEQ ID NO: 1; and
    (b) a nucleic acid molecule comprising a nucleotide sequence capable of hybridizing to a filter-bound nucleotide sequence complementary to the polypeptide coding region of a DNA molecule as defined in (a) in 0.5 H NaHPO$_4$, 7% sodium dodecyl sulfate (SDS), 1 mM EDTA at 65° C., with washing in 0.1×SSC/0.1% SDS at 68° C.

11. An isolated expression system comprising a nucleic acid molecule constituting a human GABA$_B$ receptor 1 promoter P1b set forth as SEQ ID NO: 2, or a functionally equivalent modified form thereof, or an active fragment thereof, wherein said modified form or active fragment is at least 95% homologous to said isolated molecule.

12. An expression system according to claim 11, comprising a nucleic acid molecule selected from the group consisting of:
    (a) a nucleic acid molecule comprising a nucleotide sequence set forth as SEQ ID NO: 2; and
    (b) a nucleic acid molecule comprising a nucleotide sequence capable of hybridizing to a filter-bound nucleotide sequence complementary to the polypeptide coding region of a DNA molecule as defined in (a) in 0.5 M NaHPO$_4$, 7% sodium dodecyl sulfate (SDS), 1 mM EDTA at 65° C., with washing in 0.1×SSC/0.1% SDS at 68° C.

13. An isolated expression system comprising a nucleic acid molecule according to claim 1, in combination with a nucleic acid molecule according to claim 3.

14. An isolated expression system comprising a nucleic acid molecule according to claim 2, in combination with a nucleic acid molecule according to claim 4.

15. An expression system according to any one of claims 9 to 12, which, in addition, comprises a reporter gene.

16. An expression system according to claim 15, wherein the reporter gene is selected from the group consisting of:
    (a) the firefly luciferase gene,
    (b) the bacterial chloramphenicol acetyl tranferase (CAT) gene,
    (c) the β-galactosidase (β-GAL) gene, and
    (d) the green fluorescent protein (GFP) gene.

17. An expression system according to claim 15, wherein the promoter and the reporter gene are positioned so that the expression system of the reporter gene is regulated by the GABA$_B$ receptor 1 promoter.

18. An expression system according to any one of claims 9 to 12, wherein the nucleic acid molecule is present in a vector.

19. An expression system according to claim 18, wherein said vecor comprises an origin of replication and/or a dominant selection marker.

20. An isolated host cell transfected with an expression system according to ony one of claims 9 to 12.

21. An expression system according to claim 16, wherein the promoter and the reporter gene are positioned so that the expression system of the reporter gene is regulated by the GABA$_B$ receptor 1 promoter.

* * * * *